US00PP28024P2

(12) United States Plant Patent
Koekkoek

(10) Patent No.: US PP28,024 P2
(45) Date of Patent: May 16, 2017

(54) CARNATION PLANT NAMED 'HILMIMI'

(50) Latin Name: *Dianthus caryophyllus*
Varietal Denomination: Hilmimi

(71) Applicant: Arthur N. J. Koekkoek, Alkmaar (NL)

(72) Inventor: Arthur N. J. Koekkoek, Alkmaar (NL)

(73) Assignee: Hilverda Kooij B.V., De Kwakel (NL)

( * ) Notice: Subject to any disclaimer, the term of this patent is extended or adjusted under 35 U.S.C. 154(b) by 40 days.

(21) Appl. No.: 14/545,368

(22) Filed: Apr. 28, 2015

(51) Int. Cl.
*A01H 5/02* (2006.01)

(52) U.S. Cl.
USPC ..... Plt./273

(58) Field of Classification Search
USPC ..... Plt./273
See application file for complete search history.

(56) References Cited

PUBLICATIONS

UPOV hit on *Dianthus* plant named 'Hilmimi', QZ PBR 20143567, application publication date Feb. 15, 2015.*

* cited by examiner

*Primary Examiner* — Anne Grunberg
(74) *Attorney, Agent, or Firm* — C. A. Whealy

(57) ABSTRACT

A new and distinct cultivar of Carnation plant named 'Hilmimi', characterized by its uniformly mounding and upright to broadly spreading plant habit; relatively small leaves; freely flowering habit; salmon pink-colored double flowers; and good container performance.

1 Drawing Sheet

Botanical designation: *Dianthus caryophyllus*.
Cultivar denomination: 'HILMIMI'.

BACKGROUND OF THE INVENTION

The present invention relates to a new and distinct cultivar of Carnation plant, botanically known as *Dianthus caryophyllus*, grown commercially as a container plant and hereinafter referred to by the name 'Hilmimi'.

The new Carnation plant is a product of a planned breeding program conducted by the Inventor in De Kwakel, The Netherlands. The objective of the breeding program is to create new container Carnation plants with numerous double flowers.

The new Carnation plant originated from a cross-pollination made by the Inventor in De Kwakel, The Netherlands in June, 2010 of a proprietary selection of *Dianthus caryophyllus* identified as code number A76263-02, not patented, as the female, or seed, parent with *Dianthus caryophyllus* 'Orapotse', not patented, as the male, or pollen, parent. The new Carnation plant was discovered and selected by the Inventor as a single flowering plant from within the progeny of the stated cross-pollination in a controlled greenhouse environment in De Kwakel, The Netherlands in September, 2011.

Asexual reproduction of the new Carnation plant by terminal cuttings propagated in a controlled greenhouse environment in De Kwakel, The Netherlands since October, 2011 has shown that the unique features of this new Carnation plant are stable and reproduced true to type in successive generations of asexual reproduction.

SUMMARY OF THE INVENTION

Plants of the new Carnation have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilmimi'. These characteristics in combination distinguish 'Hilmimi' as a new and distinct Carnation plant:

1. Uniformly mounding and upright to broadly spreading plant habit.
2. Relatively small leaves.
3. Freely flowering habit.
4. Salmon pink-colored double flowers.
5. Good container performance.

Plants of the new Carnation differ from plants of the female parent selection in the following characteristics:

1. Plants of the new Carnation are more freely branching than plants of female parent selection.
2. Plants of the new Carnation have shorter peduncles than plants of the female parent selection.
3. Flower petals of plants of the new Carnation have fewer and fainter dark red-colored stripes than flower petals of plants of the female parent selection.

Plants of the new Carnation differ from plants of the male parent, 'Orapotse', in the following characteristics:

1. Plants of the new Carnation have more petals per flower than plants of 'Orapotse'.
2. Flower petals of plants of the new Carnation have fewer and fainter dark red-colored stripes than flower petals of plants of 'Orapotse'.
3. Flower petals of plants of the new Carnation are more praemorse than flower petals of plants of 'Orapotse'.

Plants of the new Carnation also can be compared to plants of *Dianthus caryophyllus* disclosed in U.S. Plant patent application Ser. No. 14/120,582. In side-by-side comparisons, plants of the new Carnation differed primarily from plants of 'Hilluigi' in the following characteristics:

1. Plants of the new Carnation had smaller flowers than plants of 'Hilluigi'.
2. Flower petals of plants of the new Carnation were lighter in color than flower petals of plants of 'Hilluigi'.
3. Flower petals of plants of the new Carnation were more praemorse than flower petals of plants of 'Hilluigi'.

BRIEF DESCRIPTION OF THE PHOTOGRAPH

The accompanying photograph illustrates the overall appearance of the new Carnation plant showing the colors as true as it is reasonably possible to obtain in colored reproductions of this type. Colors in the photograph may differ slightly from the color values cited in the detailed botanical description which accurately describe the colors of the new Carnation plant.

The photograph comprises a side perspective view of a typical flowering plant of 'Hilmimi' grown in a container.

DETAILED BOTANICAL DESCRIPTION

Plants used in the aforementioned photograph and following observations and measurements were grown during the winter in 10.5-cm containers in a glass-covered greenhouse in De Kwakel, The Netherlands and under cultural practices typical of commercial container Carnation production. During the production of the plants, day temperatures ranged from 12° C. to 15° C., night temperatures averaged 12° C. and light levels averaged 7,000 lux. Plants were pinched one time five weeks after planting. Plants used for the photograph and description were twelve weeks old. In the following description, color references are made to The Royal Horticultural Society Colour Chart, 2007 Edition, except where general terms of ordinary dictionary significance are used.

Botanical classification: *Dianthus caryophyllus* 'Hilmimi'.

Parentage:

*Female, or seed, parent.*—Proprietary selection of *Dianthus caryophyllus* identified as code number A76263-02, not patented.

*Male, or pollen, parent.*—*Dianthus caryophyllus* 'Orapotse', not patented.

Propagation:

*Type.*—By terminal cuttings.

*Time to initiate roots, summer.*—About six days at temperatures ranging from 20° C. to 25° C.

*Time to initiate roots, winter.*—About eight days at temperatures about 18° C.

*Time to produce a rooted young plant, summer.*—About three weeks at temperatures ranging from 20° C. to 25° C.

*Time to produce a rooted young plant, winter.*—About five weeks at temperatures about 18° C.

*Root description.*—Medium in thickness, fibrous; whitish in color.

*Rooting habit.*—Moderate branching; medium density.

Plant description:

*Plant and growth habit.*—Herbaceous perennial, typically grown as a container plant; uniformly mounding, upright to broadly spreading plant habit; moderately vigorous growth habit.

*Plant height, soil level to top of foliar plane.*—About 16.4 cm.

*Plant height, soil level to top of floral plane.*—About 19.5 cm.

*Plant diameter or spread.*—About 22.7 cm.

*Lateral branches.*—Branching habit: Freely branching habit with about five main (basal) stems; each main stem with about three lateral branches. Length, main stems: About 10.6 cm. Length, lateral branches: About 5 cm. Diameter, main stems and lateral branches: About 2.5 mm. Internode length: About 2.1 cm. Number of internodes per stem: About three. Strength: Strong. Aspect: Main stems, mostly upright; lateral branches, about 25° from the main stem. Cross-section: Angular; solid. Texture: Smooth, glabrous; waxy. Luster: Matte. Color: Close to 137B; waxy layer, close to 189B.

Leaf description:

*Arrangement.*—Opposite, simple; sessile.

*Length.*—About 9.4 cm.

*Width.*—About 7 mm.

*Shape.*—Lanceolate.

*Apex.*—Narrowly acute.

*Base.*—Attenuate; decurrent.

*Margin.*—Entire.

*Texture, upper and lower surfaces.*—Smooth, glabrous.

*Luster, upper and lower surfaces.*—Matte.

*Venation pattern.*—Parallel.

*Color.*—Developing leaves, upper surface: Close to 143A to 143B; towards the base, close to 145A. Developing leaves, lower surface: Close to 143A to 143B; towards the base, close to 145B. Fully expanded leaves, upper surface: Close to between N137C and 189A; venation, same as lamina, close to between N137C and 189A. Fully expanded leaves, lower surface: Close to N137C to N137D; venation, close to 143A.

Flower description:

*Flower form and flowering habit.*—Terminal double flowers arranged singly, in pairs or in panicles with about five flowers each; freely flowering habit with numerous flowers developing during the flowering season; flowers face mostly upright to slightly outwardly.

*Natural flowering season.*—Flowering is continuous from the summer to late summer in The Netherlands; plants begin flowering about twelve weeks after planting.

*Postproduction longevity.*—Flowers last about ten days on the plant; flowers not persistent.

*Fragrance.*—None detected.

*Flower buds.*—Length: About 2 cm. Diameter: About 1.1 cm. Shape: Broadly elliptic; styles not extruded. Color: Close to 138C; towards the base, close to 145C.

*Inflorescence height.*—About 6.9 cm.

*Inflorescence diameter.*—About 6.6 cm.

*Flower diameter.*—About 5.3 cm.

*Flower depth.*—About 5.3 cm.

*Petals and petaloids.*—Quantity and arrangement: About 25 petals/petaloids arranged in about five whorls. Length: About 4.2 cm. Width: About 2.3 cm. Shape: Spatulate. Apex: Praemorse, strongly crinkled. Base: Acute. Margin: Entire. Texture, upper and lower surfaces: Smooth, glabrous; velvety. Luster, upper and lower surfaces: Matte. Color: When opening and fully opened, upper surface: Close to 35C and 37B; occasionally striped and blotched with close to 53C; towards the base, close to 157B to 157C. With development, color becoming closer to 39B to 39C; occasionally striped and blotched with close to 53B to 53C; towards the base, close to 157B to 157C. When opening and fully opened, lower surface: Close to 37B to 37C; occasionally slightly striped and blotched with close to 53D, 54A and 54B; towards the base, close to 157B to 157C; color does not change with development.

*Sepals*.—Quantity and arrangement: About five in a single whorl; proximal 67.5% portion of the sepals are fused into a campanulate-shaped calyx; epicalyx, adpressed to the calyx; outer lobes are roughly deltoid in shape with medium to long acuminate apices and inner lobes are roughly deltoid in shape with short to medium acuminate apices. Length: About 2.2 cm. Width, at base of "free" portion: About 8 mm. Shape: Oblong. Apex: Broadly acute. Margin: Entire. Texture, upper and lower surfaces: Smooth, glabrous. Luster, upper and lower surfaces: Matte. Color: When opening, upper surface: Close to 148D. When opening, lower surface: Close to 138B; towards the base, close to 145C. Fully opened, upper surface: Close to 148D. Fully opened, lower surface: Close to N137C; towards the base, close to 144C.

*Peduncles*.—Length: About 1.8 cm. Diameter: About 2 mm. Strength: Strong. Aspect: Erect. Texture: Smooth, glabrous; waxy. Color: Close to 137B; waxy layer, close to 189B.

*Pedicels*.—Length: About 1.2 cm. Diameter: About 2 mm. Strength: Strong. Aspect: About 20° to 25° from the peduncle axis. Texture: Smooth, glabrous. Color: Close to 137B; waxy layer, close to 189A.

*Reproductive organs*.—Stamens: Quantity: About two per flower; mostly deformed. Filament length: About 6 mm. Filament color: Close to NN155D. Anther length: About 3 mm. Anther shape: Narrowly spatulate to irregularly oblong. Anther color: Close to 161D. Pollen: None produced. Pistils: Quantity: About two per flower. Pistil length: About 9 mm. Stigma shape: Pointed, slightly curved. Stigma color: Close to 43D. Style length: About 8 mm. Style color: Close to 43D. Ovary shape: Obovoid. Ovary texture: Ribbed. Ovary color: Close to 145B; lighter towards the base. Fruits and seeds: Fruit and seed development have not been observed on plants of the new Carnation.

Disease & pest resistance: Plants of the new Carnation have not been observed to be resistant to pathogens and pests common to Carnation plants.

Temperature tolerance: Plants of the new Carnation have been observed to tolerate high temperatures about 35° C. and to be hardy to USDA Hardiness Zone 9.

It is claimed:

1. A new and distinct Carnation plant named 'Hilmimi' as illustrated and described.

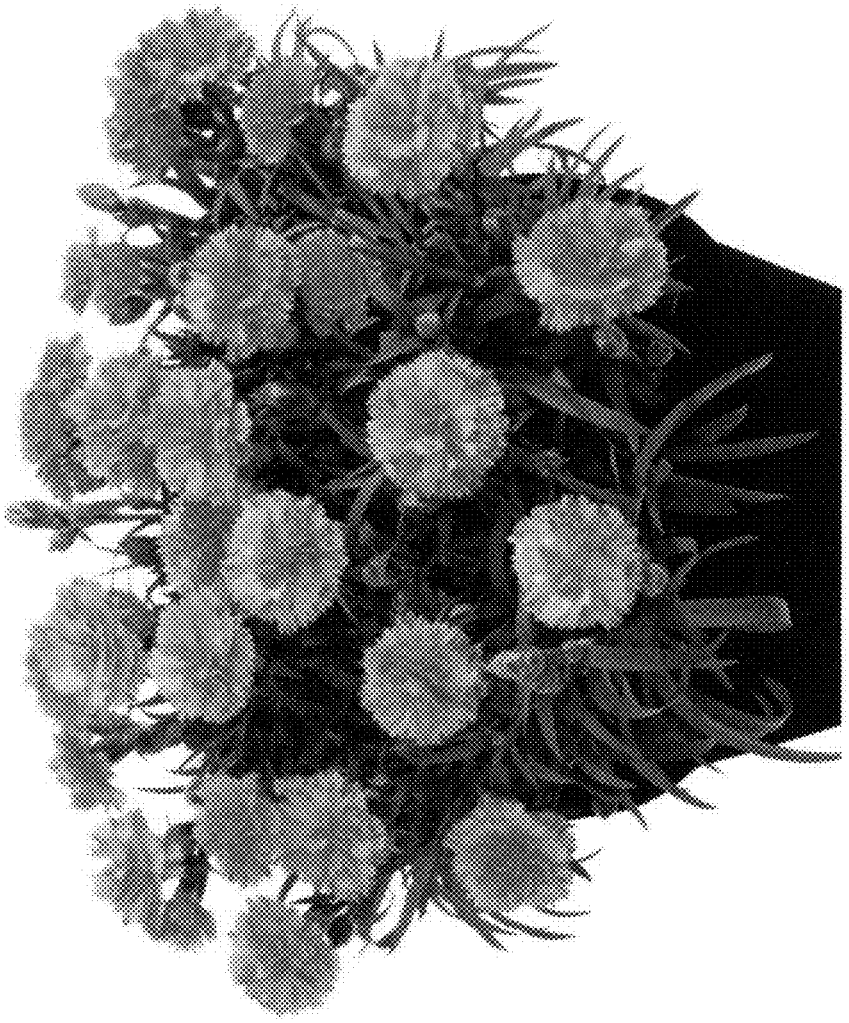

* * * * *